United States Patent [19]

Levy

[11] Patent Number: 5,424,640
[45] Date of Patent: Jun. 13, 1995

[54] METHOD FOR REMOVAL OF RANDOM NOISE IN EDDY-CURRENT TESTING SYSTEM

[75] Inventor: Arthur J. Levy, Schenectady, N.Y.

[73] Assignee: The United States of America as represented by the United States Department of Energy, Washington, D.C.

[21] Appl. No.: 58,850

[22] Filed: May 10, 1993

Related U.S. Application Data

[63] Continuation-in-part of Ser. No. 644,776, Jan. 23, 1991, abandoned.

[51] Int. Cl.[6] .................... G01N 27/90; G01R 33/12; G01R 33/10
[52] U.S. Cl. .................... 324/232; 324/238; 324/240
[58] Field of Search ............... 324/236, 243, 233, 232, 324/219, 220

[56] References Cited

U.S. PATENT DOCUMENTS

| | | | |
|---|---|---|---|
| 4,628,260 | 12/1986 | Kimoto et al. | 324/220 |
| 4,763,274 | 8/1988 | Junker et al. | 324/220 X |
| 4,806,863 | 2/1989 | White | 324/220 X |

OTHER PUBLICATIONS

*Fundamentals Of Eddy Current Testing*, by D. J. Hagemaier; Publisher: The American Society for Nondestructive Testing, Inc.; (No Month) 1990.

*Primary Examiner*—Sandra L. O'Shea
*Assistant Examiner*—Warren S. Edmonds
*Attorney, Agent, or Firm*—Thomas Zack; William R. Moser; Paul A. Gottlieb

[57] ABSTRACT

Eddy-current response voltages, generated during inspection of metallic structures for anomalies, are often replete with noise. Therefore, analysis of the inspection data and results is difficult or near impossible, resulting in inconsistent or unreliable evaluation of the structure. This invention processes the eddy-current response voltage, removing the effect of random noise, to allow proper identification of anomalies within and associated with the structure.

10 Claims, 9 Drawing Sheets

METHOD FOR REMOVAL OF RANDOM NOISE IN EDDY-CURRENT TESTING SYSTEM

RIGHTS OF THE GOVERNMENT

The invention described herein was made or conceived in the course of or under Contract No. DE-AC112-76N00052 between the U.S. Department of Energy and General Electric Company, according to which the United States Government has rights in this invention and title thereto is in the United States of America, as represented by the U.S. Department of Energy.

CROSS-REFERENCE TO RELATED APPLICATION

This application is a continuation-in-part of application Ser. No. 07/644,776 filed Jan. 23, 1991, now abandoned.

BACKGROUND OF THE INVENTION

1. Field of the Invention

The present invention relates to eddy-current testing, a non-destructive testing method for inspection of metallic structures, and, more particularly, to means for reducing noise from eddy-current defect indications to enable analysis of the electric signal to accurately and consistently evaluate the metallic structure, such as heat exchanger tubing material, being tested.

2. Background Information

Eddy-current testing is a widely used, non-destructive testing method for inspection of tubing material. The basics of eddy-current testing are set forth in *Fundamentals of Eddy Current Testing*, by D. J. Hagemaier, published by The American Society for Nondestructive Testing Inc, 1990, which is incorporated herein by reference.

The speed, sensitivity, and ease of use of eddy-current testing make it an ideal choice for inspection of heat exchanger tubing, which may be non-ferromagnetic and thin-walled. However, even in light of all the benefits associated with eddy-current testing, it is often considered one of the most frustrating non-destructive testing methods. Although the technique employed in eddy-current testing is simple and reliable, inspection data and results are frequently contradictory and misleading due to the many material variables and measurement noise which influence the eddy-current measurements. Common problems associated with eddy-current testing include inconsistent results obtained with successive inspections of the same material and inconsistent analysis of results by different analysts. As a result, confidence in the technique suffers.

Most of the difficulties associated with eddy current testing arise from the analysis of the data generated and the quality of the data. Eddy-current testing by its nature is sensitive to any change in the electrical or magnetic properties of the test part. In particular, when inspecting heat exchanger tubing, noise effects and random fluctuations caused by support structures, electrically conductive deposits, permeability variations, dents and bulges, roll expansions, and other phenomena, as well as actual defects, will be exhibited in the resulting test data. Thus, indications from these noise effects and random fluctuations frequently combine with the indications from the defects such that both the detection and sizing of flaws are compromised. In fact, present data acquisition and analysis techniques require that a human analyst recognize and quantify the defect indications imbedded in the noise which is unrelated to the defects being assessed.

An analyst, or operator, interprets eddy-current test data by viewing and inspecting visual displays of impedance plots or Lissajous patterns. The eddy-current testing measures complex impedance of the metallic object being tested. The complex impedance has a real and imaginary component which is measured as an output voltage by the instrumentation. These voltage quantities are represented by the Lissajous pattern, which is a waveform having an X-Y plot as a function of time or displacement. A typical Lissajous pattern is normally produced by recording orthogonal components of a two-dimensional process. For example, a Lissajous pattern can be produced by sampling the X and Y components of an electric field, either as a function of time or displacement. Thus, Lissajous patterns are generally two-dimensional waveforms in which real and imaginary components of successive points in a collection of data points are plotted in an X-Y plane. Such a plot forms lobes radiating from an origin with the angular position of the lobes relative to the origin representing the phase angle.

In the field of non-destructive testing, Lissajous patterns are created by passing eddy-current probes along metallic structures to detect anomalies. The Lissajous patterns revealing anomalous features are then interpreted by the analyst, or operator, who observes and analyzes significant geometric characteristics, such as phase and amplitude, and qualitative parameters, such as the fatness of a figure, to evaluate the nature of the physical structure. For example, an operator would visually inspect the Lissajous patterns in the impedance plane and identify specific pattern classes, such as a "figure-8" class or a "figure-V" class. Then, once the class is identified, the operator would determine such features as the pattern phase and amplitude, which for outside diameter defects are the quantitative measure of defect depth.

Operators have developed a highly refined ability to observe the shape and phase angle of most Lissajous patterns, such as eddy-current test patterns, and determine therefrom, with a reasonable degree of confidence, the characteristics of the two-dimensional process under observation, i.e., whether defects exist in the material being tested and the types of defects which are present. However, it must be appreciated that, for the most part, Lissajous patters are not perfect geometric patterns, and, as such, sometimes great difficulty is experienced in interpreting them either visually or with conventional pattern recognition algorithms.

Eddy-current test patterns are frequently replete with "noise". Noise is defined as curvature changes that occur along a curve's arclength that are unrelated to overall pattern appearance. For instance, a curve may oscillate rapidly, tending to confound the pattern analysis.

Three different types of noise have been identified. The first type is random noise, which is a consequence of fluctuations that occur during the measuring process. The reduction of the effect of this noise is the object of this invention. The second type of noise, called endpoint noise, is the consequence of the imprecise determination of indication limits in the data; points not associated with the indication may be included at the ends of the curves. The third type of noise may occur anywhere along a pattern curve where a small loop appears. These loops are believed to be unrelated to physical characteristics, but nonetheless display large curvature change at all levels of resolution. Pattern analysis by the operator begins after all three types of noise have been removed from the data.

In order to effectively utilize conventional visual or numerical methods to interpret features of the eddy-current test pattern which contains a relatively large component of random noise, it is apparent that the random noise should first be eliminated or substantially reduced to a relatively low level so as to smooth out the irrugular curvature of the waveform.

There are several different known prior art methods for reducing random noise fluctuations in two-dimensional waveforms. Arguably, the best of these methods uses a spline curve which is fit to a small group of points lying on the waveform. In the spline curve method, one central data point of this group is then moved to lie on the spline curve. The process is progressively moved along the waveform until all of the points have been moved. However, the spline curve method is unsatisfactory in that it removes information from the two-dimensional waveform, thus distorting it; this method results in a reduction in overall waveform quality.

Other methods for reducing random noise fluctuations in two-dimensional waveforms include one of two processes, undersampling or filtering, which remove unwanted voltage components of the eddy-current response voltage. Undersampling is a method whereby fewer samples of the eddy-current signal are made than are necessary to capture the most detailed portion of the signal. This method does not enhance the signal in any way and results in a signal generally deficient in small scale features.

Filtering is a method which imposes an a priori model of the data on the eddy-current signal. However, there is no physical reason for the imposition of any model on this type of data. Filtering methods remove information; in contrast, the present invention makes use of an oversampled signal by redistributing information to the low curvature part of the signal at the expense of the high curvature component.

Through the use of multiple-frequency eddy-current testing systems, modern equipment is capable, in principle, of acquiring the necessary data to correctly diagnose all indications. Applying consistent analysis techniques, however, is required to achieve proper evaluation of the test data. Methods in use prior to this invention do not allow consistent analysis of test data nor make use of all the information present in the data. Current data acquisition and analysis techniques require that the interpreter recognize and quantify defects imbedded in noise unrelated to the defects being assessed.

To overcome the above-mentioned obstacles, a method has been developed that effectively removes the effect of unwanted noise components of the electronic signal, allowing the defect-related portion of the signal to remain. This has the effect of making the defect pattern clear so that unambiguous analysis and diagnosis can be made. In addition, the resulting clear shape of the defect pattern enables reliable quantitative measurements of the pattern to be made.

The creation of noise-free data patterns through the present invention has enabled automatic data evaluation since computer pattern recognition methods are more likely to succeed with well formed patterns rather than with noisy ones. Machine pattern recognition, the emulation of the visual skills of an analyst, in turn, decreases the reliance on a human operator, which enhances the evaluation of eddy-current data.

Accordingly, it is a general object of the invention to provide a method for removing the effect of unwanted noise from eddy-current test signals produced during inspection of tubing material.

Another object of the present invention is to provide consistent inspection data from eddy-current tests and, thus, provide consistent and reliable evaluation of the tubing material being tested and identification of any defects present therein.

Another object of the present invention is to provide eddy-current test patterns from which quantitative measurements of the pattern can be made.

It is another object of this invention to provide an eddy-current testing system which is capable of removing the effect of unwanted noise from eddy-current test signals produced during inspection of tubing material for accurate and complete analysis of the eddy-current test measurement signals.

Other objects, advantages and novel features of the invention will be apparent to those of ordinary skill in the art upon examination of the following detailed description of a preferred embodiment of the invention and the accompanying drawings.

SUMMARY OF THE INVENTION

To achieve the foregoing and other objects and in accordance with the purpose of the present invention, as embodied and broadly described herein, a method and apparatus are provided for analyzing eddy-current response voltage produced during inspection of metallic structures. The method and apparatus allow for detection of anomalies of said metallic structures.

An eddy-current probe having two adjacent coils is passed along a metallic structure, or tubing, to generate the eddy-current response voltages of the metallic structures. The eddy-current response voltage includes random noise and is oversampled by at least a factor of 2, resulting in the response voltage being sampled at least 800 times per foot. The eddy-current probe is generally passed along the metallic structure at a rate of 1 foot per second. Thus, the sampling of the response voltage also occurs at a rate of at least 800 times per second.

A signal formation apparatus receives the eddy-current response voltage generated by the two adjacent coils of the eddy-current probe and forms a differential signal and an absolute signal. The differential signal and absolute signal are converted from analog to a digital signals. Three digital signals, having digital values, are plotted and represent X and Y arrays forming a Lissajous pattern in the impedance plane. The Lissajous pattern has a noise-induced irregular curvature which identifies a plurality of slope changes in said Lissajous pattern. The original differential and absolute signals having random noise are recorded.

The digital signal is subjected to an iteration process performed by the smooth processor to remove the effect of the random noise. A plurality of points $P_N$ (where $N=1, 2, 3 \ldots$) are selected and positioned at preselected initial locations on said irregular curvature, one of the plurality of points $P_N$ is initially located at each of said slope changes. A straight line is formed that connects each point $P_N$ to the midpoint between points $P_{(N-1)}$ and $P_{(N+1)}$. A new location is calculated for points $P_N$ on the straight line a fraction of the distance between the initial location of $P_N$ and said midpoint. These steps are repeated for each of the plurality of points $P_N$ that are positioned on the irregular curvature in succession to identify a plurality of newly calculated locations for said plurality of points $P_N$. Then, this entire process is again repeated a preselected number of times using the plurality of newly calculated point locations each time to move each point $P_N$ from its initial location and thereby identify a plurality of final calculated point locations for the plurality points $P_N$. Finally, a substantially random noise-free two-dimensional waveform, having a substantially smooth curvature, is formed by connecting said newly calculated point locations of said plurality of points $P_N$.

The substantially random noise-free two-dimensional waveform is then illustrated by a graphics display. The operator can then determine whether anomalies exist in the material being tested and the types of anomalies that are present.

DESCRIPTION OF THE PREFERRED EMBODIMENT

Figure 1:
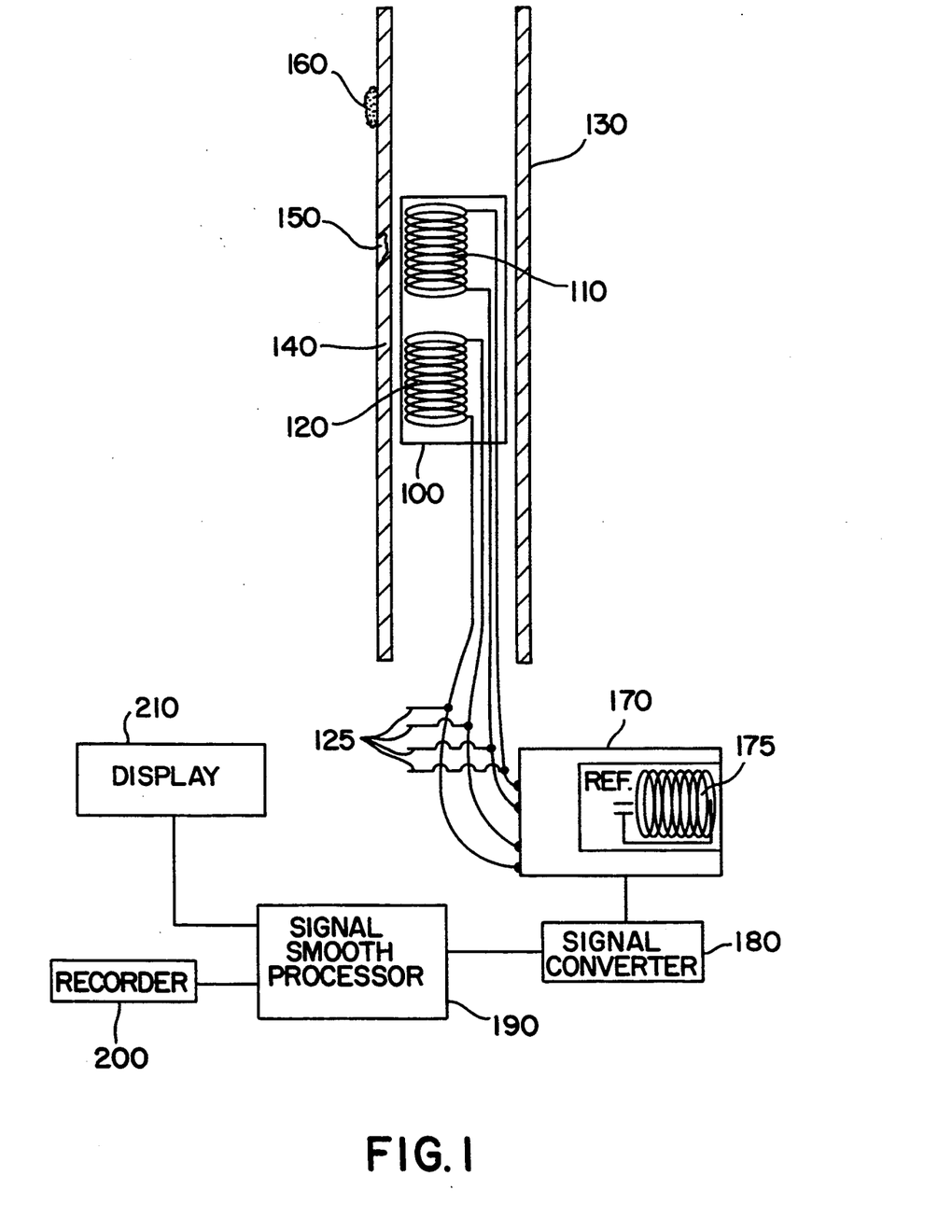
FIG. 1 is a simplified, functional, block diagram of an embodiment of the present invention.

Referring now to the drawings and particularly to FIG. 1, illustrating an eddy-current testing system in which the present invention is implemented, a dual-bobbin eddy-current probe 100, having two adjacent coils 110 and 120 therein, is passed along within a metallic tube 130 structure to detect anomalies along the metallic tube wall 140. For instance, the eddy-current probe is passed within the heat exchanger tubing to identify tubing defects. Defects to be detected may include material wall erosion 150. Likewise, the eddy-current testing system may detect an external deposit 160.

The eddy-current response voltage, or impedance, that is generated from the metallic structure is oversampled by at least a factor of two. Oversampling means that the data signals are sampled faster or more often than absolutely necessary to resolve the most detailed real, physical feature. Oversampling implies that the signals contain an overabundance of information. This invention uses the abundance of information acquired from oversampling to enhance the data-induced part of signal while reducing the random fluctuations in the signal. The prior art method of eddy-current testing provides for sampling the response voltage approximately 400 times per foot of metallic structure. The present invention samples the response voltage at least 800 times per foot, oversampling by at least a factor of two. Likewise, since the eddy-current probe is generally passed along the metallic structure at a rate of approximately 1 foot per second, the present invention samples response voltage at least 800 times per second. The best results are achieved when the response voltage is sampled approximately 1000 times per foot, which corresponds to sampling at approximately 1000 times per second.

The oversampled eddy-current response voltage, or impedance, which includes random noise, is transmitted from each coil 110, 120 through leads 125 and received by an eddy-current signal formation apparatus 170 (such as the Zetc, Inc. Model MIZ-18). The eddy-current signal formation apparatus is generally capable of generating two simultaneous signals: (1) a differential signal where the voltages generated by two adjacent coils in the probe are balanced to each other, and (2) an absolute signal where a voltage generated by a single coil 110 is balanced against a fixed reference voltage 175.

The differential signal and the absolute signal, including random noise, are fed to an analog to digital converter 180 to provide digital signals corresponding to sequential positions along the metallic structure. The output from the converter 180 is then subjected to an iteration process performed by a smooth processor 190, a microprocess. The iteration process of the smooth processor 190 removes the effect of the random noise from the signals to a desired level, providing smoothed output signals. The iteration process subjects the differential signal and the absolute signal to a prescribed number of iterations until the effect of random noise is removed to a desired level.

The differential and absolute signals output from the converter 180 are also fed to the smooth processor 190 and then stored in the recording means 200, such as a tape drive or disc memory, which is connected to the smooth processor 190. The differential and absolute signals can be retrieved from the recording means 200 for the iteration process performed by the smooth processor 190. The new values obtained for the differential and absolute signals, as the effect of the random noise is removed by the iteration process, are also stored in the recording apparatus 200.

The smooth processor 190 is also connected to a graphics display 210 or monitor which plots or displays the differential and absolute signals as two-dimensional waveforms. The two-dimensional waveform, or Lissajous pattern, that is displayed plots the X voltage and Y voltage of either the differential or absolute signal from the signal formation apparatus, which receives the voltages or distance. The Lissajous pattern to the iteration process of the smooth processor 190 generally has a random noise-induced irregular curvature or trajectory. The iteration process of the smooth processor 190 removes the effect of the random noise from the differential and absolute signals to a desired level, providing smoothed output signals which, when displayed on the graphics display 210 or monitor, form two-dimensional waveforms or Lissajous patterns having a smooth curvature. Generally, either the differential signal or the absolute signal is displayed at any one time for analysis of that waveform. Analysis of the two-dimensional waveform that is ultimately displayed yields accurate and consistent evaluation of the test material.

Figure 2:
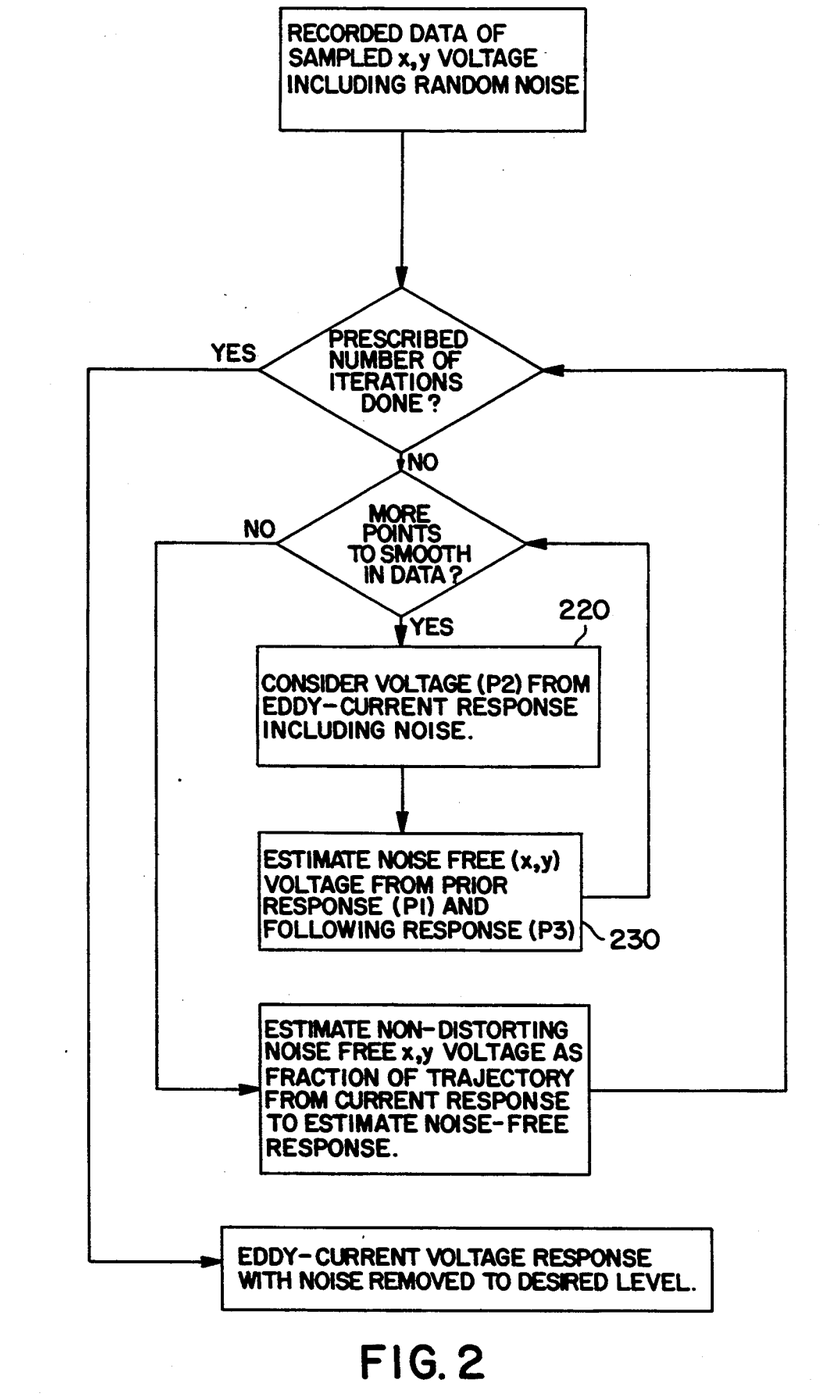
FIG. 2 is a simplified flowchart of a program used to provide an eddy-current voltage response with noise removed to a desired level.

Referring now to FIG. 2, there is illustrated a simplified flowchart of a computer program that provides an iteration routine performed by the smooth processor 190 of FIG. 1 for removal of the effects of random noise from the digitized eddy-current response signal. If the recorded signal produces a two-dimensional waveform, or Lissajous pattern, having a highly irregular curvature or jagged trajectory caused by random noise, then the data from the signal is processed to effectively remove the random noise. The data from the signal is processed by considering the voltage form one eddy-current response signal (box 220), including noise, and estimating a noise free voltage for this eddy-current response signal from the response signals immediately prior to and following the considered eddy-current response signal (box 230). A prescribed number of iterations are performed to achieve an eddy-current response with noise reduced to a desired level. The individual steps of the iteration performed by the present invention are described in further detail below in the discussion of FIG. 7.

The basis of the method is the fact that curvature changes in the two-dimensional waveform are largest when noise aberrations are greatest. Furthermore, each sampling of the curve's trajectory is most likely to be near a minimal curvature path between its two neighboring voltage sampled points, due to the oversampling of the waveform. Any given sampling of eddy-current response voltages may produce an aberrant datum. However, because of the oversampling, more is known above that data point due to the existence of its neighbors.

This method corrects aberrant samplings by enabling each voltage sampling to be coerced into its noise-free position by the effect of its neighboring voltage sampled points. In addition to the use of the neighboring voltage responses, the invention uses the knowledge that the voltage samplings are made at equal time increments. The knowledge gained from the equal time sampling is used to form an estimate of the true trajectory of the signal.

Once the prescribed number of iterations are done, resulting in an eddy-current voltage having a response with the effect of noise reduced to a desired level, a two-dimensional waveform, or Lissajous pattern, is displayed having no more data points to smooth.

Figure 3:
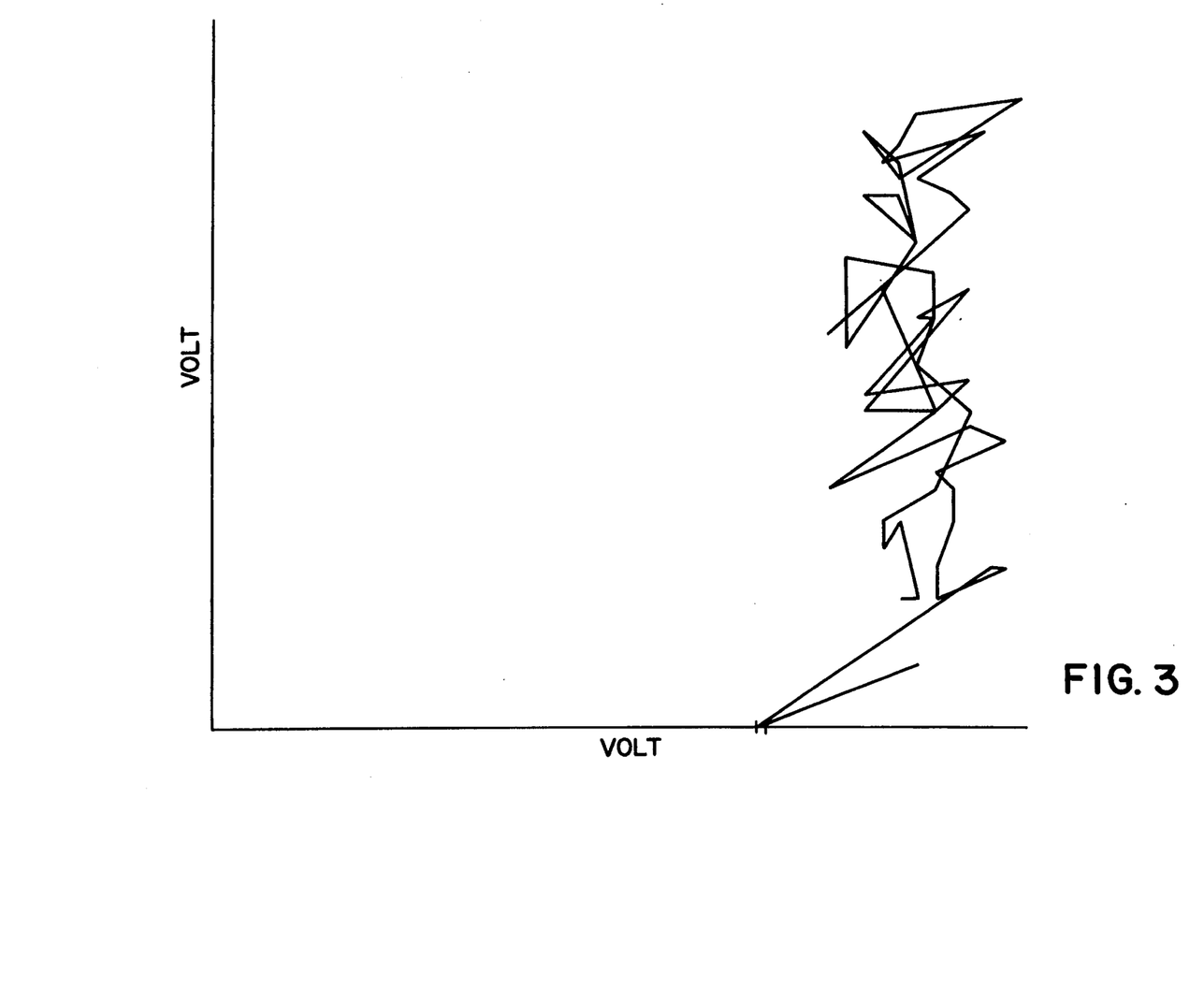
FIG. 3 is an absolute Lissajous pattern, having random noise-induced irregular curvature of trajectory, which is produced from an eddy-current response voltage caused by material wall erosion in the metallic tube being tested.

Referring now to FIG. 3, an absolute Lissajous pattern is shown, the evaluation of which will ultimately reveal material wall erosion in an area of the heat exchanger tubing being tested. (As discused above, FIG. 1 illustrates material wall erosion 150 in a metallic tube wall 140.) Absolute means that the voltage detected by a single coil of the eddy-current probe is balanced against a fixed reference voltage. Note the highly irregular curvature or jagged trajectory of the waveform, which is due to random noise within the response signal. The interpretation of this pattern is difficult for an anlayst.

Figure 4:
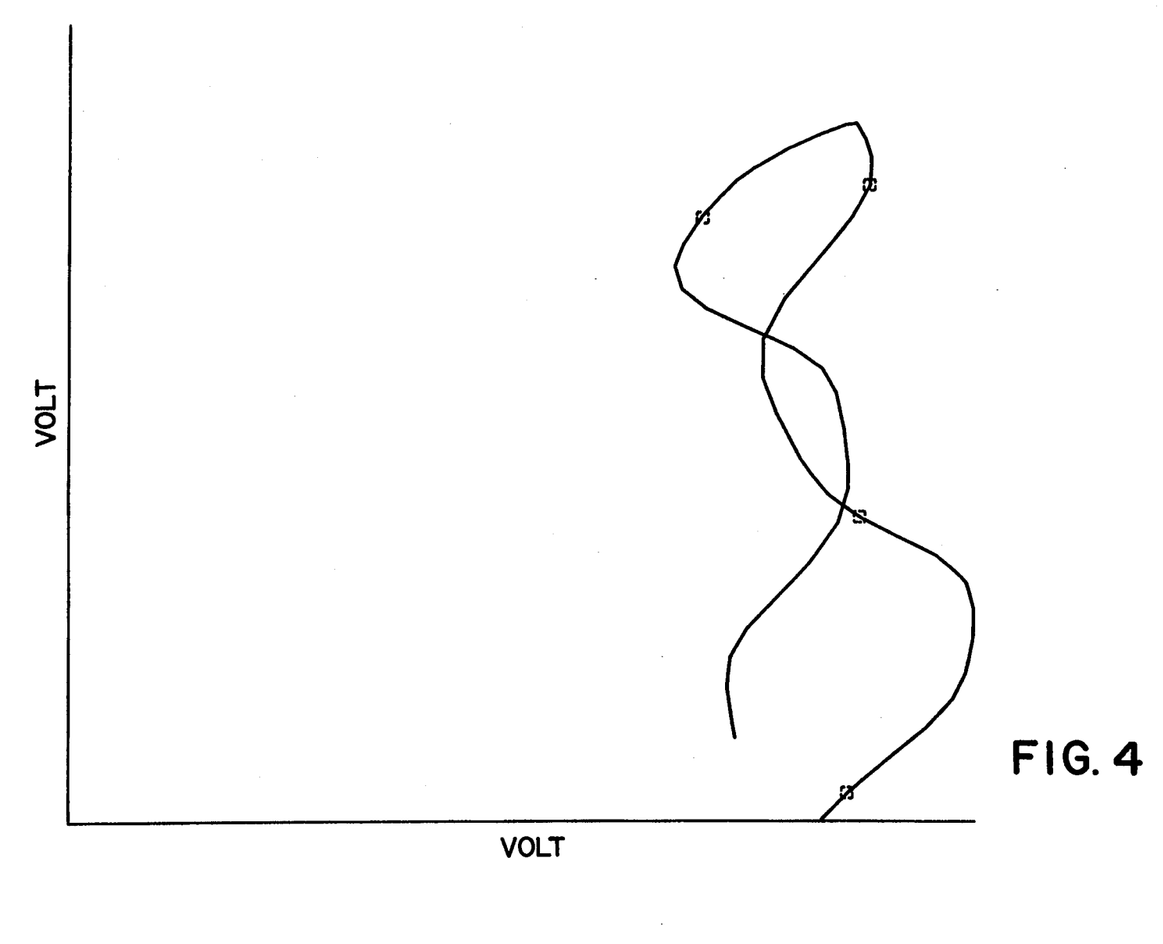
FIG. 4 is the absolute Lissajous pattern of FIG. 3 after removal of the effects of the random noise through the use of the present invention.

Turning to FIG. 4, this is the absolute Lissajous pattern of FIG. 3 after removal of the effects of the random noise through the use of the present invention. The response signal has been subjected to the iteration process of the present invention. Note the characteristic vertically-oriented loop, which is indicative of material wall erosion.

A comparison of FIGS. 3 and 4 demonstrates the effectiveness of the present invention in removing the effect of unwanted noise components of the electronic signal, allowing the defect-related portion of the signal to remain, when in turn, allows unambiguous analysis and diagnosis to be made.

Figure 5:
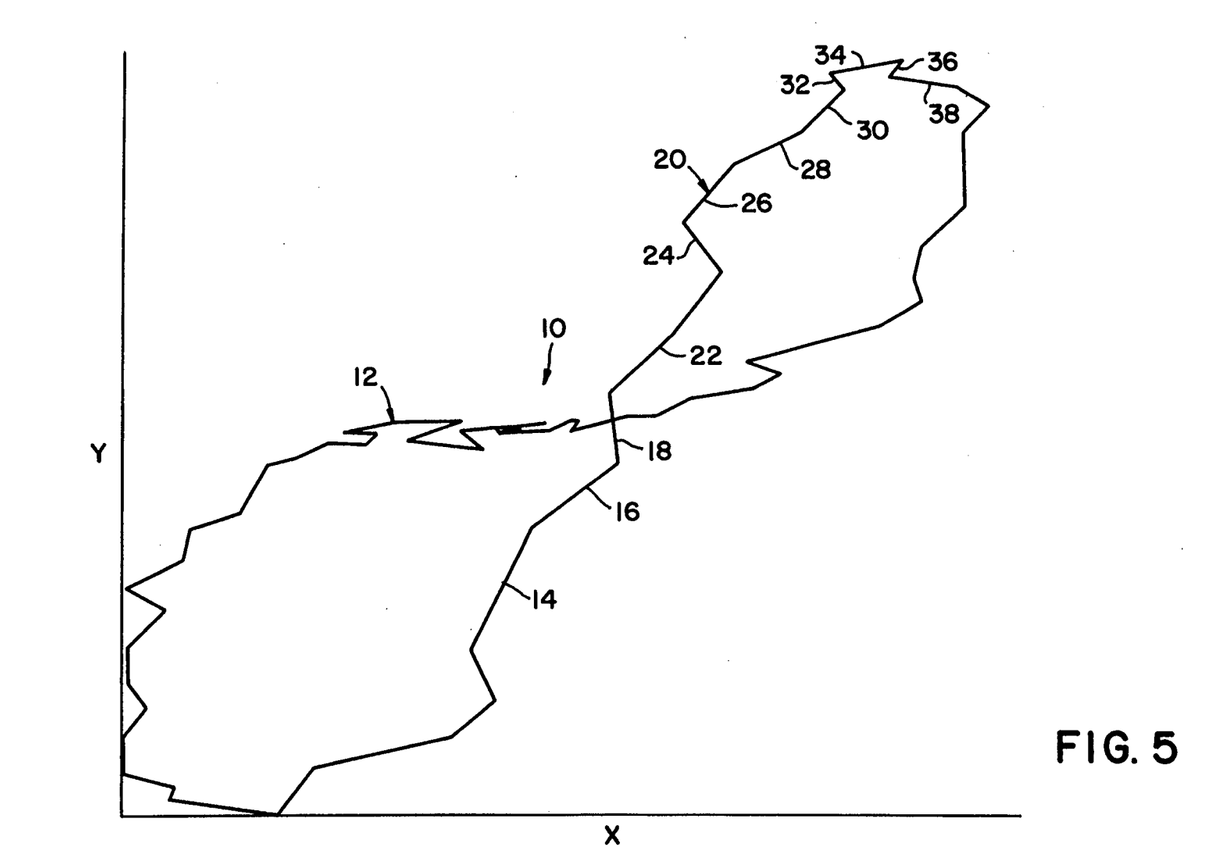
FIG. 5 is a differential Lissajous pattern, having a noise-induced irregular curvature, which results from a simulated material wall erosion, i.e., a drilled hole in the tubing material.

Turning to FIG. 5, a differential Lissajous pattern, having a noise-induced irregular curvature, is shown. This differential Lissajous pattern is caused by a simulated material wall erosion in an area of heat exchanged tubing; a hole was drilled into the tubing. Differential means that the voltage signals, from the two adjacent coils within the eddy-current probe, are balanced to each other. Theoretically, a drilled hole, simulating material wall erosion, is expected to produce a differential Lissajous pattern having a perfect "figure-8" pattern. As shown in this figure, the signal noise is quite apparent due to the irregular curvature or jagged trajectory. A waveform portion 20, a segment of waveform 10, includes a plurality of surfaces 18, 228 24, 26, 28, 30 and 32, each having a different slope.

Figure 6:
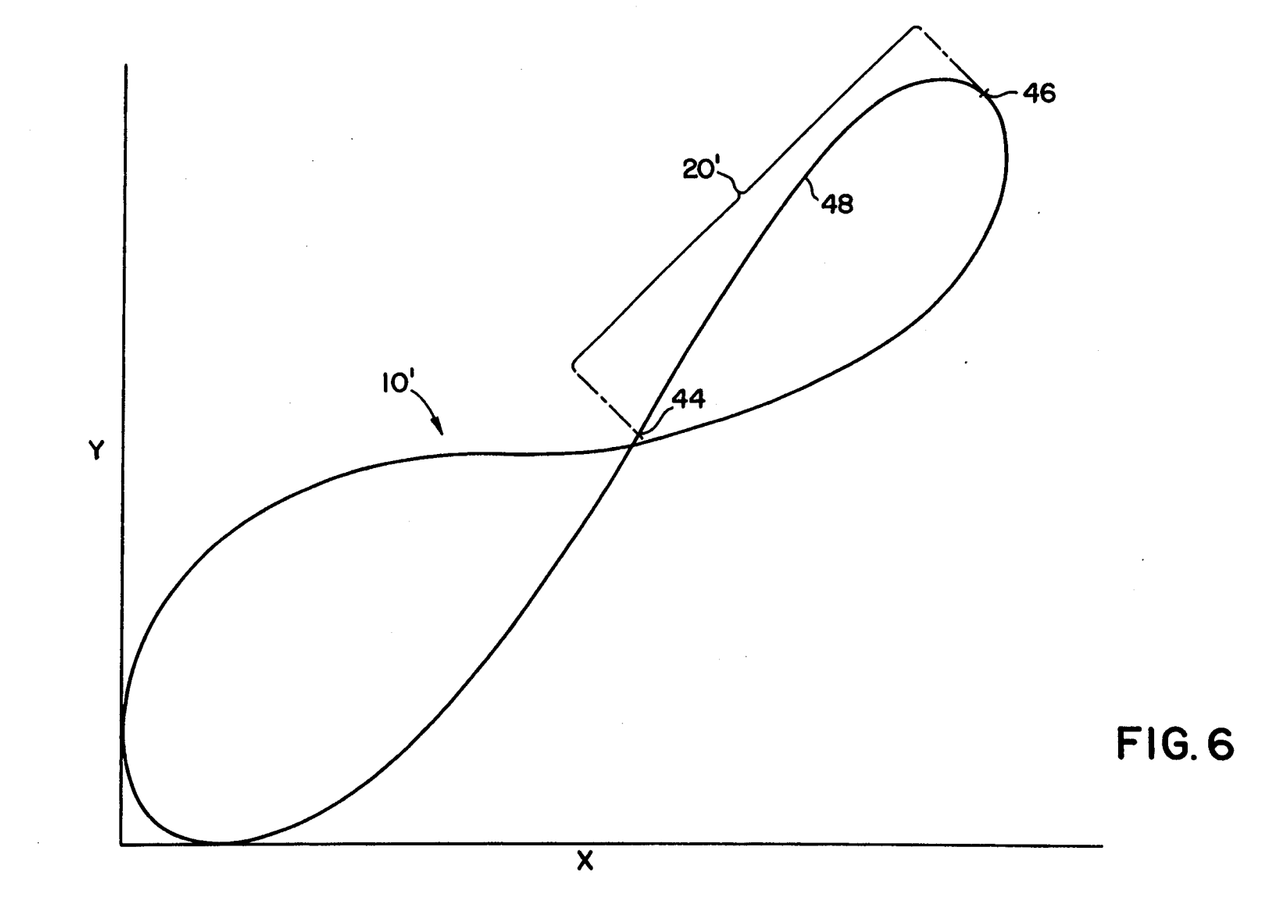
FIG. 6 is the differential Lissajous pattern of FIG. 5 after removal of the effects of random noise through the use of the present invention.

FIG. 6 shows the differential Lissajous pattern of FIG. 5 after removal of the effects of random noise through the use of the present invention. The result is the classic trajectory having no distortion as to its orientation or shape, which is crucial to quantifying the magnitude of the material removed from the metallic structure. No other method is capable of removing noise without distorting these parameters.

Figure 7:
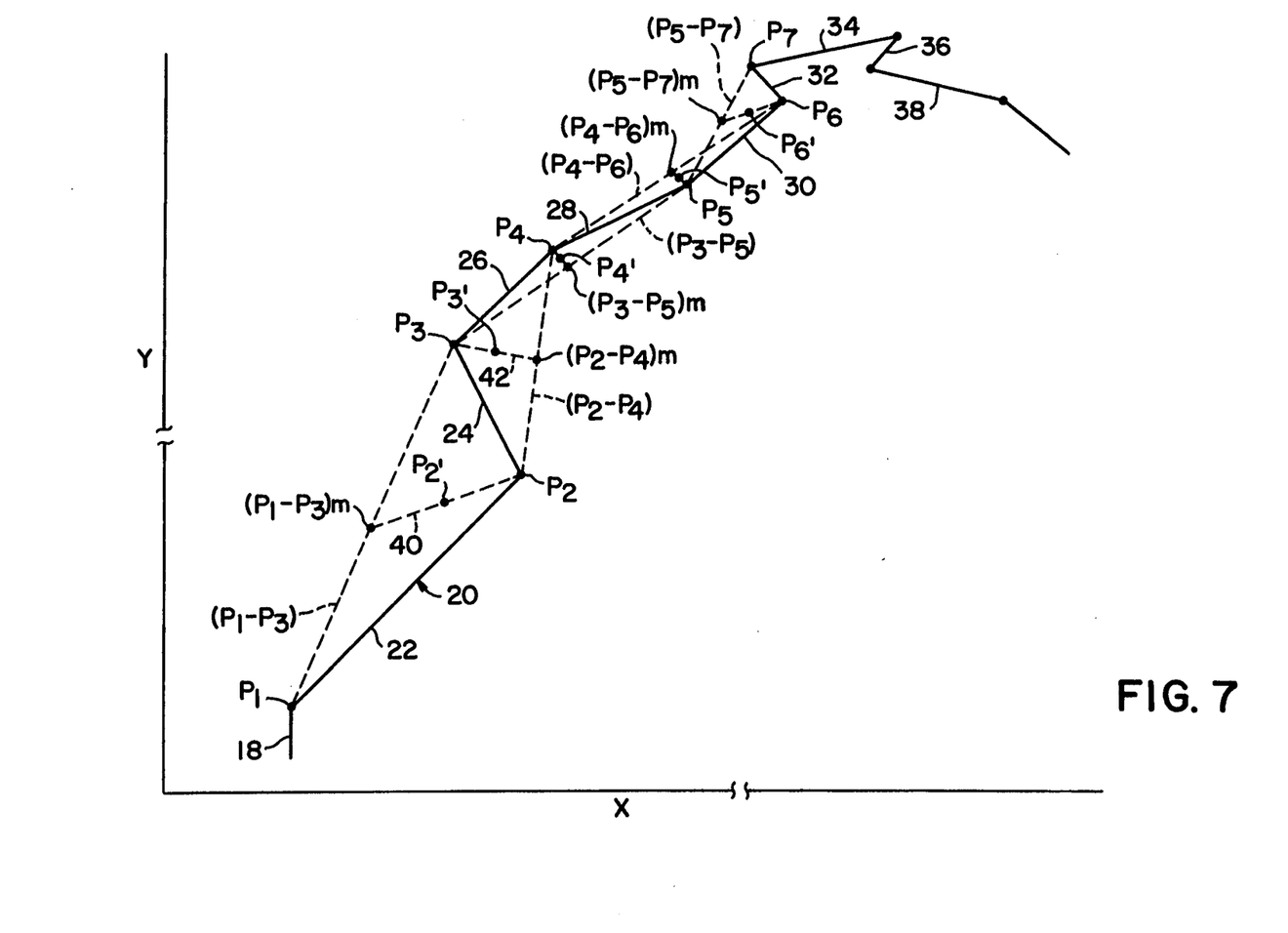
FIG. 7 is an enlarged view of a portion of the differential Lissajous pattern of FIG. 5, illustrating the method of the present invention by which the effects of random noise are removed.

FIG. 7 is an enlarged view of a portion of the differential Lissajous pattern of FIG. 5, illustrating the method of the present invention by which the effects of random noise are removed. The waveform portion 20 has been enlarged for clear illustration and explanation of the random noise-reducing method of the present invention. It should be understood that, for the sake of brevity, the method of the present invention is described herein as being applied only to waveform portion 20; however, in actual practice, this method is applied to the entire waveform 10.

As seen in FIG. 7, the waveform portion 20 includes a plurality of surfaces 18, 22, 24, 26, 28, 30, and 32, each having a different slope. The surfaces 18 and 22 intersect at a point $P_N = P_1$ and surfaces 22 and 24 intersect at a point $P_N = P_2$. In like fashion, adjacent pairs of neighboring surfaces (24, 26), (26, 28), (28, 30) and (30, 32) intersect at respect points $P_3$, $P_4$, $P_5$ and $P_6$. Thus, points $P_1$ through $P_6$ are selected to coincide with slope changes along the portion 20 of the irregular curvature 12 of the waveform 10. The locations of points $P_1$ through $P_6$ are referred to as their initial locations and it will become apparent that these initial locations will change in response to the application of the noise-reducing method described herein.

In order to practice the method for reducing the effects of random noise on the waveform 10 in accordance with the principles of the present invention, a point, such as $P_2$ is first selected. (It should be understood that point $P_2$ has only been selected as a starting point for ease in describing and demonstrating the present invention, however, in actual practice, any point on the irregular curvature 12 of the waveform 10 may be selected as the initial starting point.) Then a straight line, being designated as ($P_1$-$P_3$) is drawn connecting points $P_1$ and $P_3$, the neighboring points adjacent to point $P_2$.

Next, the midpoint of line ($P_1$-$P_3$) is found, being designated as ($P_1$-$P_3$)m. The reason that the midpoint of line ($P_1$-$P_3$) is chosen is that, in this case, it is known from prior information that the waveform was sampled at regular, equal intervals. It is this additional knowledge of how the waveform was sampled that will be used to enhance that resultant signal. Any other information of how the signal sampling interval was determined may be used to substitute that function for the midpoint. This is how the present invention adds information to the signal, thus reducing the ratio of noise to signal amplitude.

Next, a straight line 40 is found which connects point $P_2$ with the midpoint ($P_1$-$P_3$)m. Now, a new location is calculated for $P_2$ on line 40 a fraction of the distance between the initial location of point $P_2$, located at the intersection of surfaces 22 and 24, and the midpoint ($P_1$-$P_3$)m. This new location of point $P_2$ is illustrated in FIG. 7 as point $P_2'$. It has been found through experimentation that the optimum new location for point $P_2$, designated $P_2'$, is found by using a fraction of between one-third and one-half the distance from the initial location of point $P_2$ and, preferably, in a direction towards the midpoint ($P_1$-$P_3$)m.

After the new location of point $P_2$ is determined to be point $P_2'$, the steps described above are repeated for each of the remaining points $P_3$ through $P_6$ on the portion 20 on the waveform 10. For example, the new location of point $P_3$ is determined by first drawing a straight line ($P_2$-$P_4$) connecting points $P_2$ and $P_4$, the neighboring points adjacent to point $P_3$. The midpoint of line ($P_2$-$P_4$) is found and designated as ($P_2$-$P_4$)m. A straight line 42 is then found which connects point $P_3$ with the midpoint ($P_2$-$P_4$)m. A new location is now calculated for point $P_3$ on line 42 a fraction of the distance between the initial location of $P_3$, at the intersection of surfaces 24 and 26, and the midpoint ($P_2$14 $P_4$)m. This new location of point $P_3$ is illustrated in FIG. 7 as point $P_3'$. As described above with respect to point $P_2'$, new point $P_3'$ is calculated by using one-third to one-half the distance along line 42 from the initial location of point $P_3$ and in a direction towards the midpoint ($P_2$-$P_4$)m.

In like fashion, the new locations for each of the points $P_4$ through $P_6$ initially positioned on the portion 20 of the irregular curvature 12 are found. Since every slope change of waveform 10 is designated by a point $P_N$, creating a plurality of points $P_N$ initially located on the irregular curvature 12, it is apparent that one complete iteration of the method disclosed herein will generate a plurality of new locations for the plurality of points $P_N$. Each of the points $P_N$ is thus coerced along a path starting at its initial location at a curvature slope change towards the midpoint of its neighboring or adjacent points. Since the locations of the neighboring points are also uncertain due to random noise, this midpoint is not truly initially known. However, the iteration method described herein reduces the influence of uncertain neighboring point locations on the estimated destination of each point since the new location of each point is determined independently of the new locations of its neighboring points.

Once a single iteration of the method disclosed herein is complted, the entire process is repeated a desired number of times using the plurality of newly calculated point locations each time to eventually move each point $P_N$ from its initial location along the irregular curvature 12 of waveform 10 to a final calculated point location. After a plurality of final calculated locations for the plurality of points $P_N$ is determined, the final locations of the points are connected to form a relatively random noise-free two-dimensional waveform 10' having a substantially smooth curvature such as that shown in FIG. 6. For illustration purposes, the resultant waveform portion 20' is represented on FIG. 6 by the curve extending between points 44 and 46.

It has been found through experimentation that the above-described process should be repeated between twenty-five and one hundred times, depending upon the severity of the irregularities in the waveform curvature. From a comparison of FIGS. 5 and 6, it is shown that the resultant waveform 10' with its generally smooth curvature or trajectory 48, as shown in FIG. 6, is approximately the same as the irregular waveform 10 with its jagged curvature 12, as shown in FIG. 5; however, the resultant waveform 10' has the random noise component, or the effect of random noise, removed in accordance with the principles of the present invention.

Figure 8:
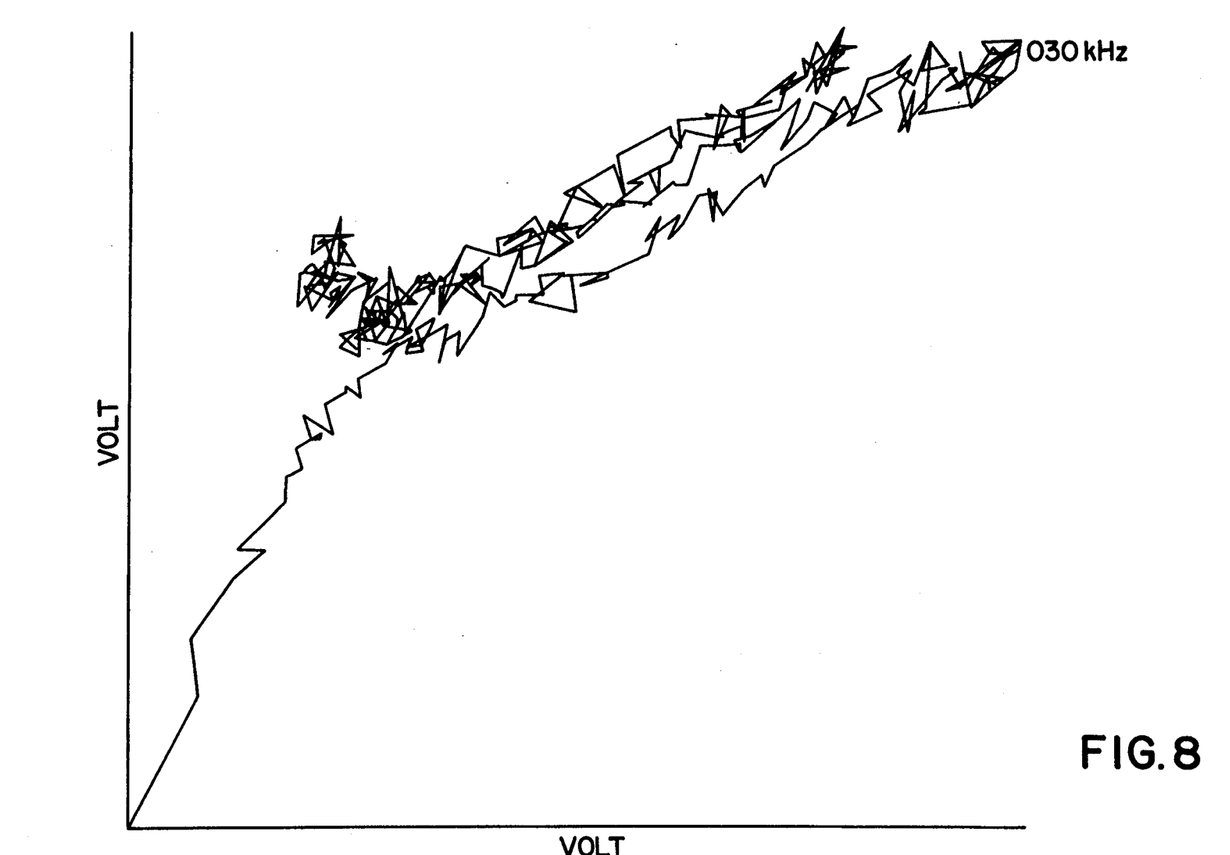
FIG. 8 is an absolute Lissajous pattern, having a noise-induced irregular curvature, which is caused by the deposit of material on the outside of a metallic tube being generated by an eddy-current probe from within the tube.

For further illustration of the present invention reference is now made to FIG. 8, which shows an absolute Lissajous pattern, having random noise-induced irregular curvature or trajectory, that results from material that is deposited on the outside of a metallic tube. By pulling the eddy-current probe through the metallic tubing, the outside of the tubing, which cannot otherwise be observed, is evaluated.

Figure 9:
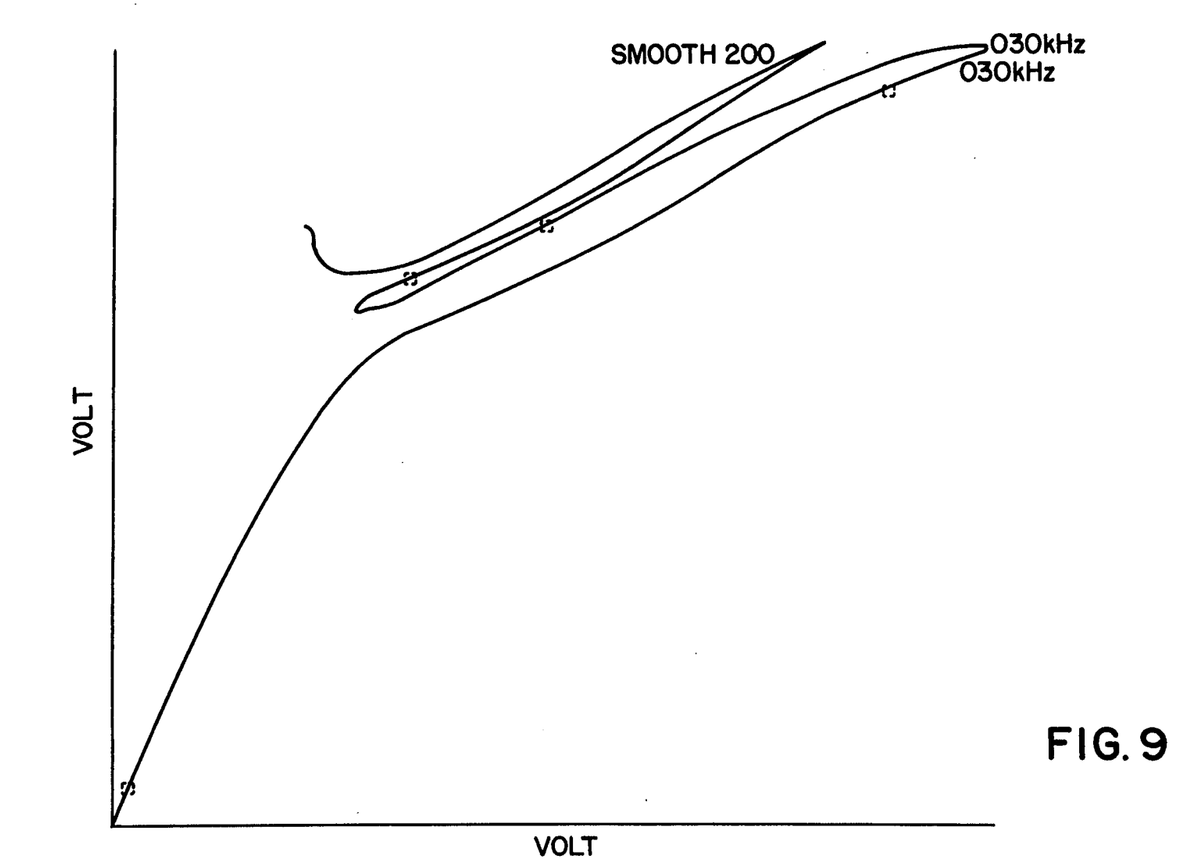
FIG. 9 is the absolute Lissajous pattern of FIG. 8 after removal of the effects of random noise through the use of the present invention.

When material is deposited on the outside of the metallic tube, an analyst should recognize two excursions of the signal, indicating two separate deposits. However, these features are obliterated in FIG. 8 due to the presence of random noise. FIG. 9 shows the absolute Lissajous pattern of FIG. 8 after removal of the effects of the random noise through the use of the present invention. After the removal of the effects of random noise from the signal, it becomes possible to both recognize and quantify the effect of the material deposit on the outside of the metallic tube.

The foregoing description of a preferred embodiment of the invention has been presented for purposes of illustration and description; it is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. While the invention has been illustrated with respect to specific hardware, it should be understood that alternative general or specific purpose equipment or hard wired logic circuitry could be used in practicing the invention.

What is claimed is:

1. A method to reduce random noise and improve graphical results obtained from eddy-current response voltages produced during inspection of metallic structures, said method allowing for detection of anomalies of said metallic structures, said method comprising the steps of:

(a) passing an eddy-current probe along said metallic structures to generate at least two eddy-current response voltages, said eddy current probe further including two coils, whereby said eddy-current response voltages are oversampled and include random noise;

(b) forming a differential signal and an absolute signal with an eddy-current formation device from the generated eddy-current response voltages;

(c) converting said differential signal and said absolute signal from analog to digital signals, thereby providing signals having digital values which, when ploted, represent X and Y arrays forming a Lissajous pattern in the impedance plane, said Lissajous pattern having a noise-induced irregular curvature, said irregular curvature identifying a plurality of slope changes in said Lissajous pattern;

(d) selecting a plurality of points Pn (where n=1,2,3 ... ) positioned at preselected initial locations on said irregular curvature, one of said plurality of points Pn initially located at each of said slope changes;

(e) finding a straight line connecting each point Pn to the midpoint between points P(n−1) and P(n+1);

(f) calculating a new location for points Pn on said straight line a fraction of the distance between the initial location of Pn and said midpoint;

(g) repeating steps (e) and (f) for each of said plurality of points Pn positioned on said irregular curvature in succession to identify a plurality of newly calculated locations for said plurality of points Pn;

(h) repeating steps (e), (f) and (g) a preselected number of times using the plurality of newly calculated point locations each time to move each point Pn from its initial location and thereby identify a plurality of final calculated point locations for said plurality points Pn;

(i) providing a substantially random noise-free two dimensional waveform having a substantially smooth curvature by connecting said newly calculated point locations of said plurality of points Pn; and (j) displaying said substantially random noise-free two dimensional waveform to permit the analysis thereof.

2. The method of claim 1, wherein step (h) is repeated between twenty-five and one hundred times.

3. The method of claim 1, wherein said fraction of the distance between the initial location of $P_N$ and said midpoint of step as set forth in step (f) falls within a range of between one-third to one-half the distance from the initial location of $P_N$ towards said midpoint.

4. The method of claim 3, wherein step (h) is repeated between twenty-five and one hundred times.

5. The method of claim 1, wherein said oversampling results in the sampling of the response voltages at least approximately 800 times per foot of metallic structure.

6. The method of claim 1, wherein said oversampling results in the sampling of the response voltages at least approximately 800 times per second.

7. The method of claim 1, wherein said oversampling results in the sampling of the response voltages approximately 1000 times per foot of metallic structure.

8. The method of claim 1, wherein said oversampling results in the sampling of the response voltages approximately 1000 times per second.

9. The method of claim 4, wherein said oversampling results in the sampling of the response voltages approximately 1000 times per foot of metallic structure.

10. The method of claim 4, wherein said oversampling results in the sampling of the response voltages approximately 1000 times per second.

* * * * *